United States Patent [19]

Harju et al.

[11] Patent Number: 4,760,055

[45] Date of Patent: Jul. 26, 1988

[54] GROWTH-STIMULATING ANIMAL FEED, A PROCESS FOR PREPARING IT, AND AN ADDITIVE TO BE USED IN IT

[75] Inventors: Matti E. Harju, Nummela; Jouko J. Setälä, Espoo; Matti K. Heikonen, Espoo; Eero P. Linko, Espoo, all of Finland

[73] Assignee: Valio Meijerien Keskusosuusliike, Helsinki, Finland

[21] Appl. No.: 893,244

[22] Filed: Aug. 5, 1986

[51] Int. Cl.$^4$ .............................................. G08C 18/08
[52] U.S. Cl. ................................................... 514/53
[58] Field of Search .............. 426/2, 61, 807; 424/93; 514/53, 23; 536/4.1

[56] References Cited

U.S. PATENT DOCUMENTS

| 3,957,976 | 5/1976 | Sugimoto | 514/513 |
| 3,973,050 | 8/1976 | Hayashibara et al. | 426/658 |
| 4,442,132 | 4/1984 | Kim | 426/658 |

FOREIGN PATENT DOCUMENTS

| 0039981 | 11/1981 | European Pat. Off. | 536/4.1 |
| 002338 | 8/1980 | Fed. Rep. of Germany . | |
| 8401491 | 4/1984 | France . | |
| 0060957 | 4/1983 | Japan | 426/2 |
| 0133547 | 2/1985 | Japan . | |
| 2113998 | 8/1983 | United Kingdom . | |
| 0858721 | 8/1981 | U.S.S.R. | 426/2 |

OTHER PUBLICATIONS

Masuda, "Feed Additive or Feed" Derwent Abstract of Japanese Patent 58-51852, Mar. 26, 1983.
Publication, Carbohydrate Sweeteners in Foods and Nutrition, Edited by Koivistoinen and Hyvonen Press, 1980, pp. 243-257, Article "Lactitol" by Linko, et al.
Nutritive Sweeteners, Edited by Birch and Parker, Applied Science, 1982, pp. 109-131, Article Entitled "Lactose and Lactitol" by Linko.

Primary Examiner—R. B. Penland
Attorney, Agent, or Firm—Cushman, Darby & Cushman

[57] ABSTRACT

The invention relates to a lactitol-containing feed which stimulates the growth of monogastric domestic animals, especially calves.

4 Claims, No Drawings

GROWTH-STIMULATING ANIMAL FEED, A PROCESS FOR PREPARING IT, AND AN ADDITIVE TO BE USED IN IT

The present invention relates to a growth-stimulating feed for monogastric domestic animals, especially calves, a process for preparing it, and an additive to be used in it.

Various derivatives, such as lactulose and lactitol, can be prepared chemically from lactose. Lactulose, i.e. 4$\beta$-D-galactosyl-D-fructose is a synthetic disaccharide, which can be prepared from lactose by heat treatment under alkaline conditions. Lactulose does not break down in the small intestine of man, since the $\beta$-galactosidase secreted by the intestinal wall is not capable of breaking down lactulose. For this reason, lactulose can pass further into the intestines, where bacteria ferment it into acids. The pH in the intestines drops, the growth of proteolytic bacteria slows down, and the intestinal flora turns lactic acid predominant. However, other sugars and alcohols which are not absorbable from the intestines have not been observed to have an equally definite effect. Lactulose thus has a specific growth-stimulating effect on lactic acid bacteria.

For the above-mentioned reasons, lactulose has been used as a drug for patients with encephalopathy or constipation, in mother's milk substitutes to convert the intestinal flora so as to correspond to feeding with mother's milk, but also a growth-stimulating effect on domestic animals has been observed. The effect is based on improved utilization of protein as the proteolysis and deamination due to instestinal bacteria are decreased. Susceptibility to diarrhea is also reduced.

The preparation of lactulose from lactose is, however, difficult (yield only about 20%), and owing to strong secondary reactions the purification further increases costs. For this reason, the possibilities for using lactulose in animal feeds are limited.

According to the invention, it has now surprisingly been observed that by using the other lactose derivative, i.e. lactitol, a similar or even better growth-stimulating effect is achieved in the feeding of monogastric domestic animals, especially calves. Furthermore, the preparation of lactitol from lactose is easier (yield nearly 100%), and impurities due to secondary reactions are hardly produced.

Lactitol, i.e. 4$\beta$-D-galactosyl-D-sorbitol is a synthetic sugar alcohol which can be prepared by hydrating lactose or a lactose-containing solution (e.g. whey or an ultrafiltrate of whey) under suitable conditions. The preparation and properties of lactitol are described in, for example, the following article: Linko, P., Saijonmaa, T., Heikonen, M. and Kreula, M., Lactitol, in Carbohydrate Sweeteners in Foods and Nutrition, Eds. Koivistoinen, P. and Hyvönen, L., Academic Press, London, 1980.

Uses have been proposed for lactitol mainly as a low-calorie sweetener (e.g. DE Pat. No. 2 133 428, U.S. Pat. No. 3,973,050, and U.S. Pat. No. 4,442,132). It has also been claimed that lactitol reduces the level of cholesterol in the blood (U.S. Pat. No. 3,957,976), and it has been suggested as a drug for the treatment of liver diseases (GB Pat. No. 2 113 998).

The bifidogenic action of lactitol in infants has also been mentioned (FR Pat. No. 1 317 216). From lactitol it is possible to prepare fatty acid esters (e.g. JP Pat. No. 75 013 771 and U.S. Pat. No. 3,951,945), which have been claimed to be suitable emulsifiers and stabilizers for, for example toothpastes, foods, and animal feeds (JP Pat. Nos. 55 092 310, 56 062 536, 56 097 215, 56 118 012, and 58 060 943). Fatty acid esters of sugar alcohols have also been claimed to improve the digestibility of nutrients in animal and fish feeds (JP Pat. No. 58 051 852).

The main characteristics of the invention are given in the accompanying claims.

The invention is based on the fact that an addition of lactitol to the feed of a monogastric domestic animal e.g. a calf, improves the growth of the animal. The advantageous amount of lactitol in feed is such that the animal receives lactitol daily over 1 g/kg metabolic live weight and less than 4 g/kg metabolic live weight.

The feed to which lactitol is added is a feed ordinarily used for feeding of animals, possibly containing conventional additives such as lactic acid bacteria, e.g. *Lactobacillus acidophilus*, vitamins, antibiotics, etc.

The stimulating action of lactulose on lactic acid bacteria, deviating from the action of other unabsorbable carbohydrates, was noted above. Since it is a prerequisite for the utilization of lactulose and lactitol in bacterial cells that the $\beta$-galactosidase produced by the bacterium breaks it down to fructose and galactose, or respectively to sorbitol and galactose, the differences in the specificity of the $\beta$-galactosidases of different geni of bacteria may explain the lactic acid bacteria favoring effect. The properties of the $\beta$-galactosidase of the small intestine of monogastric animals, e.g. calves, may also differ from the $\beta$-galactosidase of the small intestine of man.

The following experiment series was carried out to investigate the matter.

The $\beta$-galactosidase activity was determined from the villi of the small intestine of man and of calf by using lactose, lactulose and lactitol as the substrate. The results are shown in Table 1.

TABLE 1

Relative activities of the $\beta$-galactosidases of the villi of the small intestine of man and of calf, and of certain bacteria, in the hydrolysis of lactulose and lactitol, as compared with lactose.

| | Relative acitivity (%) | | |
| --- | --- | --- | --- |
| | Lactose | Lactulose | Lactitol |
| Man | 100 | 0 | 0 |
| Calf | 100 | 0 | 0 |
| *Lactobacillus acidophilus* | 100 | 100 | 96 |
| *Bidifobacterium longum* | 100 | 96 | 95 |
| *Bacteroides fragilis* | 100 | 9 | 8 |
| *Escherichia coli* | 100 | 8 | 2 |

The $\beta$-galactosidases of man and of calf do not hydrolyse lactulose and lactitol at all. Lactitol can thus pass further into the intestines without being absorbed. Typical intestinal lactic acid bacteria, such as *L. acidophilus* and *B. longum*, are capable of hydrolysing lactulose and lactitol as rapidly as lactose, but the typical intestinal proteolytic bacteria, such as *B. fragilis* and *E. coli* break down lactulose, and especially lactitol, very slowly as compared with lactose. This gives the lactic acid bacteria a significant growth advantage, since $\beta$-galactosidase activity is in general, even on a lactose substrate, a factor which limits the growth rate of bacteria.

Calf was selected as the experimental animal for the feeding experiment, since at the fatling stage calves often suffer from growth disturbances and diarrhea, for which reason antibiotics are often added to commercial fattening feeds.

In the use of lactitol it is very important to administer a suitable dosage, since too small a dose does not produce the desired effect and too large an amount is laxative. In the preliminary experiments it was observed that the suitable dosage level is 1.0–4.0 g lactitol/kilogram metabolic live weight ($W^{0.73}$). The actual feeding experiment is described in Example 1.

EXAMPLE 1

In the experiment carried out in practice on a farm there were 24 calves, which were divided into three groups of eight calves each. The groups were made as equal as possible on the basis of the initial weights of the calves. The experiment lasted for four weeks, and the calves received a commercial fattening feed 500 g/calf/d. Furthermore, the calves of group 2 were given lactulose 2.0 g/kg $w^{0.73}$ in the form of a 50% syrup, and the calves of group 3 were given lactitol 2.35 g/kg $w^{0.73}$ in the form of lactitol monohydrate powder mixed with the fattening feed. The growth results are shown in Table 2.

TABLE 2

Effect of lactitol on the growth of calves during the fattening period.

|  | Control | Lactulose | Lactitol |
|---|---|---|---|
| Calves/group | 8 | 8 | 8 |
| Mean initial weight, kg | 47.5 | 47.1 | 48.1 |
| Mean growth rate (g/d) |  |  |  |
| 0–2 weeks | 361 | 425 | 445 |
| 0–4 weeks | 475 | 540 | 582 |

The calves of the lactitol group grew clearly better than those of the control group, and better even than those of the group which received lactulose.

The following examples illustrate some milk replacer compositions intended for calves.

Composition 1

| Skimmilk powder | 35 | % by weight |
|---|---|---|
| Delactosed whey powder | 40.5 | % by weight |
| Fat | 14 | % by weight |
| Minerals and vitamins | 4 | % by weight |
| Lactitol | 6.5 | % by weight |

Composition 2

| Skimmilk powder | 30 | % by weight |
|---|---|---|
| Buttermilk powder | 9 | % by weight |
| Whey powder | 23.5 | % by weight |
| Soybean meal | 14 | % by weight |
| Fat | 15 | % by weight |
| Lecitin, minerals and vitamins | 2 | % by weight |
| Lactitol | 6.5 | % by weight |

We claim:
1. A growth-stimulating feed for monogastric domestic animals comprising a feed ordinarily used for the feeding of said animals and lactitol in such an amount that the animal receives daily 1 g to 4 g lactitol per kg metabolic live weight whereby a growth stimulating effect is achieved in the feeding of said monogastric domestic animals.

2. A feed according to claim 1 further comprising *Lactobacillus acidophilus.*

3. A feed according to claim 1 further comprising vitamins.

4. A feed according to claim 1 wherein said feed is a fattening feed for calves.

* * * * *